United States Patent
Zhou et al.

(10) Patent No.: US 11,877,949 B2
(45) Date of Patent: Jan. 23, 2024

(54) TURBINE-WORM TRACTION DEVICE APPLIED TO IMPLANTED TONGUE TRACTION DEVICE

(71) Applicants: Xing Zhou, Guangdong (CN); Xiangmin Zhang, Guangdong (CN)

(72) Inventors: Xing Zhou, Guangdong (CN); Xiangmin Zhang, Guangdong (CN)

(*) Notice: Subject to any disclaimer, the term of this patent is extended or adjusted under 35 U.S.C. 154(b) by 970 days.

(21) Appl. No.: 16/610,634

(22) PCT Filed: Jan. 5, 2017

(86) PCT No.: PCT/CN2017/070315
§ 371 (c)(1),
(2) Date: Nov. 15, 2019

(87) PCT Pub. No.: WO2017/121282
PCT Pub. Date: Jul. 20, 2017

(65) Prior Publication Data
US 2020/0179158 A1   Jun. 11, 2020

(30) Foreign Application Priority Data

Jan. 13, 2016 (CN) .......................... 201610024498.4
Jan. 4, 2017 (CN) .......................... 201710005657.0

(51) Int. Cl.
*A61F 5/56* (2006.01)
*A61F 2/08* (2006.01)

(52) U.S. Cl.
CPC ................ *A61F 5/566* (2013.01); *A61F 2/08* (2013.01); *A61F 2002/0894* (2013.01); *A61F 2250/0012* (2013.01)

(58) Field of Classification Search
CPC .... A61F 2/08; A61F 5/56; A61F 5/566; A61F 2250/0004–0008; A61F 2250/0012;
(Continued)

(56) References Cited

U.S. PATENT DOCUMENTS 5,885,283 A    3/1999 Gittleman
6,119,400 A *  9/2000 Ovenshire ............... F16H 19/06
                                                 74/89.22
(Continued)

FOREIGN PATENT DOCUMENTS

CN    204863623 U    12/2015
CN    204863624 U    12/2015
(Continued)

OTHER PUBLICATIONS

Zhou, Xing, International Search Report and Written Opinion, PCT/CN2017/070315, dated Mar. 28, 2017, 9 pgs.

*Primary Examiner* — Rachael E Bredefeld
*Assistant Examiner* — Trisha Talapatra
(74) *Attorney, Agent, or Firm* — Morgan, Lewis & Bockius LLP

(57) ABSTRACT

A worm gear-worm retractor for an implanted tongue retraction device is provided. The retractor of the present invention includes a control switch capable of adjusting a retraction force of a pull line, a pull line fixing device capable of fixing the pull line, and a casing. The control switch and the pull line fixing device are mounted in the casing, and the control switch is a worm gear-worm structure formed by a worm and a worm gear. Because the control switch adopts the worm gear-worm structure, by rotating the worm, the worm gear can be driven, so that the pull line fixing device connected to the worm gear rotates, thereby tensioning or loosening the pull line to adjust the retraction force of the pull line fixing device. The retractor has advantages of a compact structure, a small size and convenient adjustment.

13 Claims, 10 Drawing Sheets

(58) Field of Classification Search
CPC .......... F16H 1/16; F16H 55/22; F16H 1/1225;
A61B 2017/0404; A61B 2017/248
USPC .................. 128/848, 860; 602/29–30, 37
See application file for complete search history.

(56) References Cited

U.S. PATENT DOCUMENTS

| | | | |
|---|---|---|---|
| 11,000,403 B2* | 5/2021 | Zhou | ......................... A61F 2/00 |
| 2006/0235264 A1 | 10/2006 | Vassallo | |
| 2008/0021263 A1* | 1/2008 | Escude | ................. A61F 2/0045 |
| | | | 600/29 |
| 2008/0135056 A1* | 6/2008 | Nelissen | ................. A61F 5/566 |
| | | | 128/848 |
| 2012/0123196 A1* | 5/2012 | Rion | .................... A61F 5/0053 |
| | | | 600/37 |
| 2016/0374766 A1* | 12/2016 | Schuh | ................. A61B 5/4523 |
| | | | 606/130 |
| 2017/0296376 A1* | 10/2017 | Zhou | ........................ A61F 5/566 |

FOREIGN PATENT DOCUMENTS

| | | |
|---|---|---|
| CN | 205598077 U | 9/2016 |
| WO | WO 2015/104190 A1 | 7/2015 |

* cited by examiner

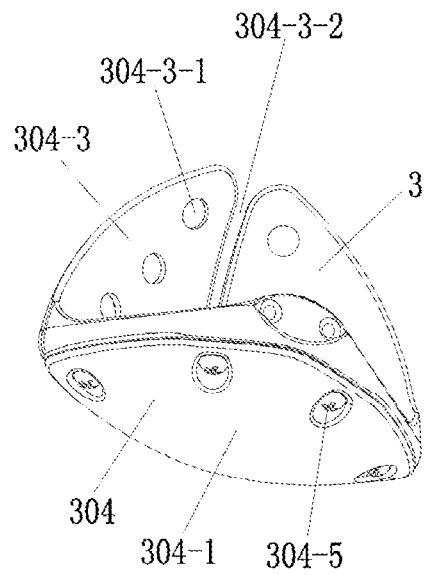
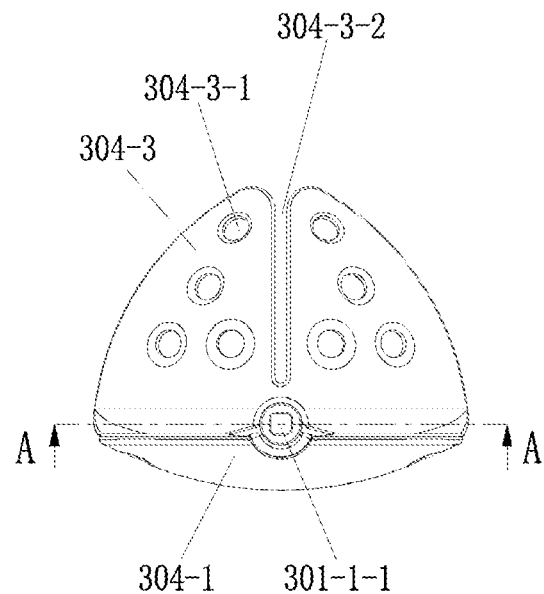
FIG. 1
FIG. 2
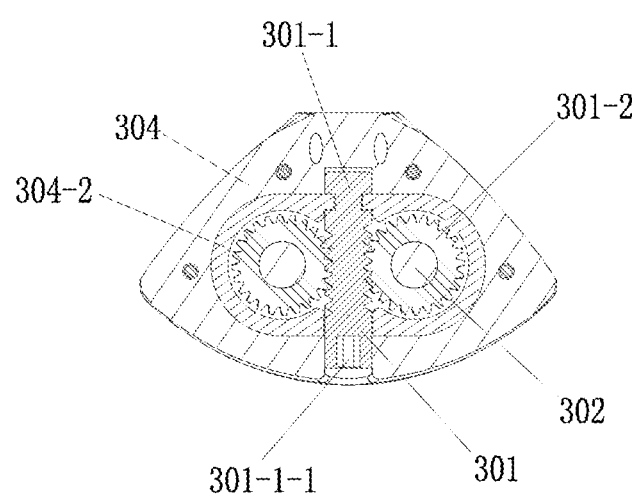
FIG. 3

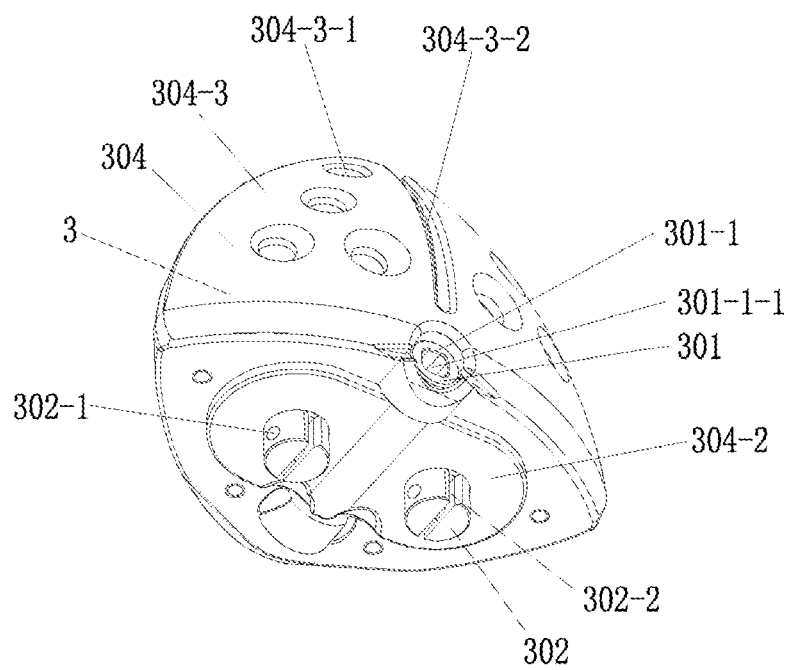
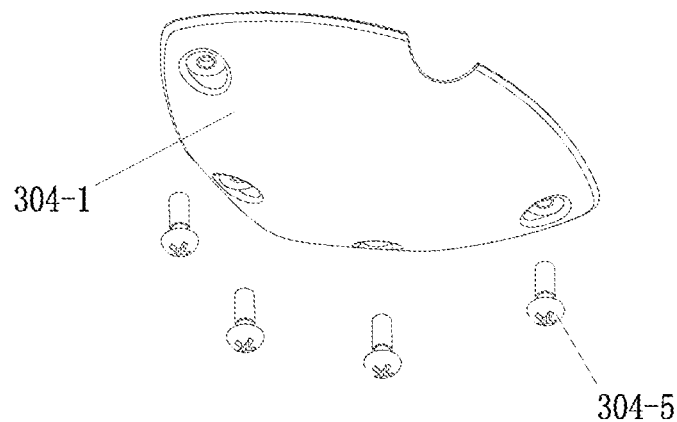
FIG. 4

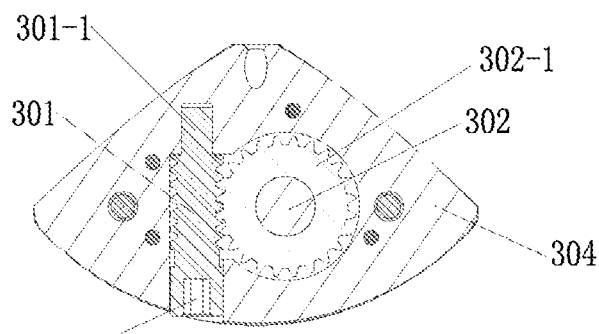
FIG. 6
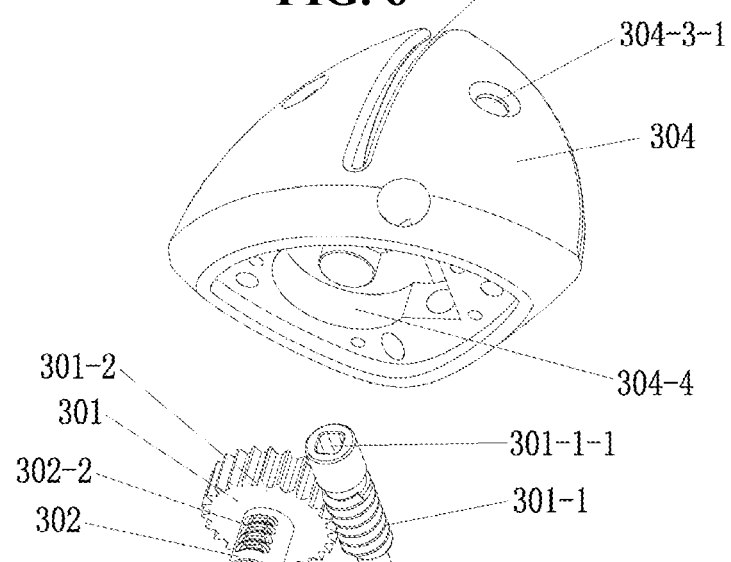
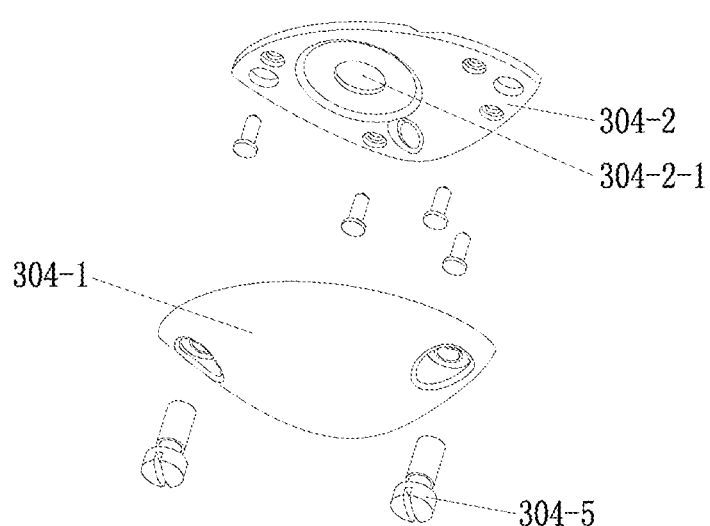
FIG. 7

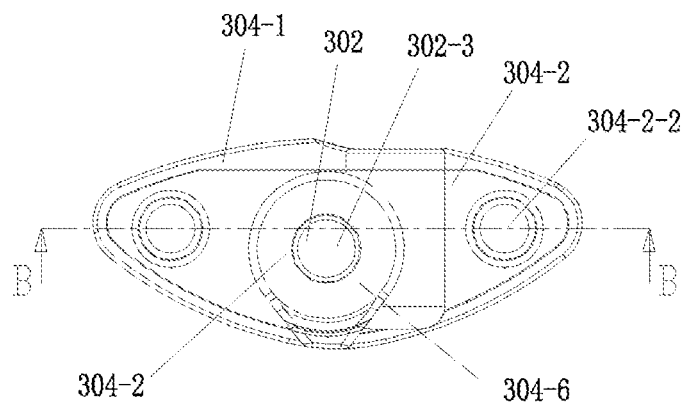
FIG. 11
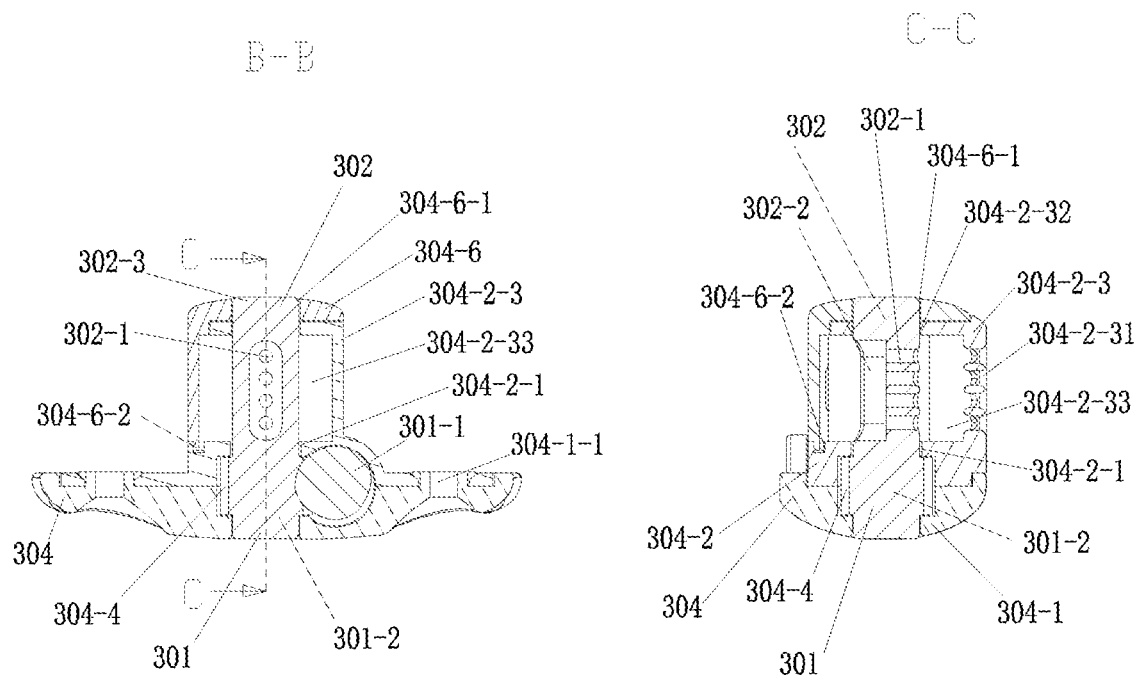
FIG. 12 · FIG. 13

TURBINE-WORM TRACTION DEVICE APPLIED TO IMPLANTED TONGUE TRACTION DEVICE

CROSS REFERENCE TO RELATED APPLICATIONS

This Application is a United States National Stage Application filed under 35 U.S.C. § 371 of PCT Patent Application Serial No. PCT/CN2017/070315 filed on Jan. 5, 2017, which claims the benefit of and priority to Chinese Patent Application No. 201710005657.0 filed on Jan. 4, 2017, which are hereby incorporated by reference in their entirety.

FIELD OF THE INVENTION

The present invention relates to a worm gear-worm retractor for an implanted tongue retraction device, and in particular, to a retractor of an implanted tongue retraction device used to treat snoring and obstructive sleep apnea/hypopnea syndrome (OSAHS for short below).

BACKGROUND OF THE INVENTION

The obstructive sleep apnea/hypopnea syndrome (OSAHS) is a disease of sleep breathing disorder with clinical features of snoring, apnea and hypopnea caused by soft tissue collapse and obstruction of an upper airway during sleep.

As for pathogenesis, it is generally considered that the OSAHS is a result of multiple factors. In addition to stenosis of the anatomical structure of the upper airway, a main cause is that pharyngeal muscles for maintaining the upper airway open relax during sleep, resulting in soft tissue collapse and obstruction. The obstruction often occurs on the palatopharyngeal plane or the glossopharyngeal plane.

Studies show that 20% to 25% of OSAHS patients are caused purely by soft tissue collapse of the palatopharyngeal plane, 15% to 20% of the OSAHS patients are caused purely by soft tissue collapse of the glossopharyngeal plane, and 50% to 70% of the OSAHS patients have soft tissue collapse of the palatopharyngeal plane and the glossopharyngeal plane at the same time, that is, mixed OSAHS patients.

In order to treat the OSAHS induced by the soft tissue collapse of the glossopharyngeal plane caused by glossoptosis, the inventor disclosed an implanted tongue base retraction device in Chinese Patent Application CN102198010A. The invention has a good therapeutic effect clinically, and is particularly suitable for surgical treatment for patients with moderate or severe OSAHS caused by tongue base collapse.

This patent application is a further improvement and perfection of the retractor of the implanted tongue retraction device of the above-mentioned patent application.

SUMMARY

A worm gear-worm retractor for an implanted tongue retraction device is provided. The retractor 3 includes a control switch 301 capable of adjusting a retraction force of a pull line 2, a pull line fixing device 302 capable of fixing the pull line 2, and a casing 304; the control switch 301 and the pull line fixing device 302 are mounted in the casing 304; where the control switch 301 is a worm gear-worm structure formed by a worm 301-1 and a worm gear 301-2; the worm gear 301-2 is driven to rotate clockwise or counter-clockwise by rotating the worm 301-1; and the pull line fixing device 302 is disposed on the worm gear 301-2; and furthermore, the casing 304 includes an inner cover 304-2; the control switch 301 is mounted on the casing 304 through the inner cover 304-2, and the pull line fixing device 302 connected to the worm gear 301-2 extends out of a through hole 304-2-1 on the inner cover 304-2. In this technical solution that uses the exposed pull line fixing device 302 and the built-in worm gear and worm, on the one hand, it is convenient to mount the pull line 2, and on the other hand, protected by the inner cover 304-2, the worm gear-worm structure is mounted in a mounting slot between the casing 304 and the inner cover 304-2, so a risk that the pull line 2 is twisted off by the worm gear-worm structure because of slippage and displacement is avoided.

The casing 304 includes a bottom cover 304-1, and the control switch 301 and the pull line fixing device 302 are mounted in the bottom cover 304-1.

The control switch 301 includes at least one worm gear 301-2 and at least one worm 301-1.

The control switch 301 includes two worm gears 301-2 and one worm 301-1; when the worm 301-1 rotates in a right-hand screw direction, a worm gear on a right side rotates clockwise, and a worm gear on a left side rotates counter-clockwise, to tension the pull line 2, so that the retraction force increases; when the worm 301-1 rotates in a left-hand screw direction, the worm gear on the right side rotates counter-clockwise, and the worm gear on the left side rotates clockwise, to loosen the pull line 2, so that the retraction force decreases.

The worm 301-1 has an adjustment hole 301-1-1, and the adjustment hole 301-1-1 is non-circular. The adjustment hole 301-1-1 is usually a polygonal hole, for example, a triangular hole, a square hole, a pentagonal hole, or a hexagonal hole. The worm 301-1 can be rotated by using a special screwdriver inserted in the adjustment hole 301-1-1.

The pull line fixing device 302 includes a fixing through hole 302-1 for fixing the pull line 2 and a line slot 302-2, and a center line of the fixing through hole 302-1 is crossed with the line slot 302-2 in a three-dimensional manner. Usually, the center line of the fixing through hole 302-1 can be perpendicular to the line slot 302-2.

The casing 304 includes a mandible front fixing plate 304-3; the mandible front fixing plate 304-3 has a front screw through hole 304-3-1 through which a fixing screw 10 passes and a slot hole 304-3-2; the slot hole 304-3-2 divides the mandible front fixing plate 304-3 into a left side and a right side. Because the slot hole 304-3-2 is disposed, the mandible front fixing plate 304-3 may be applicable to different mandibular shapes, have a good shape adjustment effect, and facilitate fixing of the mandible front fixing plate 304-3 on a mandible 5 by using the fixing screw 10, so that the retractor 3 is fixed on the mandible 5.

During assembly, firstly, the control switch 301 formed by the worm gear 301-2 and the worm 301-1 is mounted in a mounting slot 304-4 of the casing 304. Secondly, the inner cover 304-2 is mounted, and the pull line fixing device 302 connected to the worm gear 301-2 extends out through the through hole 304-2-1 on the inner cover 304-2. Finally, the bottom cover 304-1 is fixed on the casing 304 by using a screw 304-5 to complete the assembly of the retractor 3.

When the retractor 3 is used clinically, under local anesthesia, firstly, through an oral cavity, a traction plate 1 is implanted in a tongue body 9 near a glossopharyngeal portion by cutting a small incision at a tongue dorsum portion. Then, a small incision of approximately 6 mm is cut at a bottom portion of the mandible 5, the mandible front fixing plate 304-3 of the retractor 3 is fixed on the mandible 5 by using the fixing screw 10 similar to a bone screw structure, that is, the retractor 3 is fixed on the mandible 5; in this case, the mandible front fixing plate 304-3 is in front of the mandible 5, and a main body of the retractor 3, that is, the casing 304 mounted with the worm gear-worm structure, is suspended at the bottom portion of the mandible 5. Next, the pull line 2 is guided by a special instrument, through the tongue body 9, from the traction plate 1 implanted in the tongue body 9 at the tongue dorsum portion to a vicinity of the small incision in the mandible 5.

The pull line 2 is mounted and fixed on the pull line fixing device 302 connected to the worm gear 301-2 after the bottom cover 304-1 of the casing 304 is removed. The fixing through hole 302-1 and the line slot 302-2 of the pull line fixing device 302 can firmly connect the pull line 2 to the pull line fixing device 302. At this time, in the tongue body 9, one end of the pull line 2 is connected to the traction plate 1, and the other end of the pull line 2 is connected to the pull line fixing device 302 of the retractor 3.

Finally, the bottom cover 304-1 is remounted on the casing 304 by using the screw 304-5, suturing the incision, so as to complete a clinical implantation of the worm gear-worm retractor for the implanted tongue retraction device of the present invention.

When the retraction force of the pull line 2 needs to be adjusted, a special screwdriver 4 with a head shape matching a shape of the adjustment hole 301-1-1 is selected. After the special screwdriver 4 perforates skin of the mandible, the head of the special screwdriver 4 is inserted in the adjustment hole 301-1-1, and the special screwdriver 4 is turned, so that the worm 301-1 of the control switch 301 is rotated to drive the worm gear 301-2 to rotate. Thus, the pull line 2 is loosened or tensioned to adjust the retraction force of the pull line 2. When the worm 301-1 rotates in the right-hand screw direction, the worm gear on the right side rotates clockwise, and the worm gear on the left side rotates counter-clockwise, to tension the pull line 2, so that the retraction force increases; when the worm 301-1 rotates in the left-hand screw direction, the worm gear on the right side rotates counter-clockwise, and the worm gear on the left side rotates clockwise, to loosen the pull line 2, so that the retraction force decreases.

The control switch 301 includes one worm gear 301-2 and one worm 301-1; when the worm 301-1 rotates in the right-hand screw direction, the worm gear 301-2 rotates clockwise to tension the pull line 2, so that the retraction force increases; when the worm 301-1 rotates in the left-hand screw direction, the worm gear 301-2 rotates counter-clockwise to loosen the pull line 2, so that the retraction force decreases.

The casing 304 includes the upper cover 304-6; the upper cover 304-6 has an alignment hole 304-6-1. The alignment hole 304-6-1 matches a size with an end portion 302-3 of the pull line fixing device 302.

The bottom cover 304-1 has a bottom screw through hole 304-1-1 through which the fixing screw 10 passes.

The inner cover 304-2 further has a mounting hole 304-2-2 through which a fixing screw 10 passes and a positioning end 304-2-3 at which the pull line fixing device 302 is positioned; the positioning end 304-2-3 has a pull line through hole 304-2-31 through which the pull line 2 passes and a positioning hole 304-2-32 through which the pull line fixing device 302 is positioned; the pull line fixing device 302 connected to the worm gear 301-2 is mounted in a mounting slot 304-2-33 of the positioning end 304-2-3 after extending out through the through hole 304-2-1 on the inner cover 304-2, and is positioned through the positioning hole 304-2-32.

During assembly, firstly, the control switch 301 formed by the worm gear 301-2 and the worm 301-1 is mounted in a mounting slot 304-4 of the casing 304, and an adjustment hole 301-1-1 of the worm 301-1 is aligned with an adjustment through hole 304-1-2 of the bottom cover 304-1. Then, the inner cover 304-2 is mounted, after the pull line fixing device 302 connected to the worm gear 301-2 extends out through the through hole 304-2-1 on the inner cover 304-2, the pull line fixing device 302 is mounted in the mounting slot 304-2-33 of the positioning end 304-2-3, and is positioned through the positioning hole 304-2-32. Then, the alignment hole 304-6-1 on the upper cover 304-6 is aligned with the end portion 302-3 of the pull line fixing device 302, covering the upper cover 304-6, a positioning plate 304-6-2 of a bottom end of the upper cover 304-6 is inserted in an upper cover mounting slot 304-2-4 of the inner cover 304-2 to complete an assembly of the retractor 3.

When the retractor 3 is used clinically, under local anesthesia, firstly, through an oral cavity, the traction plate 1 is implanted in a tongue body 9 near a glossopharyngeal portion by cutting a small incision at a tongue dorsum portion. Then, a mounting slot having a width of about 6 mm and a depth of about 6 mm is cut in a middle portion of the mandible 5, and the retractor 3 is fixed on the mandible 5 through the through hole 304-1-1 on the bottom cover 304-1 and the mounting hole 304-2-2 on the inner cover 304-2 by using the fixing screw 10 similar to a bone screw structure. In this case, the pull line fixing device 302 connected to the worm gear 301-2 and the positioning end 304-2-3 of the inner cover 304-2 are embedded in a mounting slot in front of the mandible 5, and other parts of the retractor 3 are suspended at a bottom portion of the mandible 5. Next, the pull line 2 is guided by a special instrument, through the tongue body 9, from the traction plate 1 implanted in the tongue body 9 at the tongue dorsum portion to a vicinity of the small incision in the mandible 5.

The pull line 2 is mounted and fixed on the pull line fixing device 302 connected to the worm gear 301-2 after the bottom cover 304-6 of the casing 304 is removed. The fixing through hole 302-1 and the line slot 302-2 of the pull line fixing device 302 can firmly connect the pull line 2 to the pull line fixing device 302. At this time, in the tongue body 9, one end of the pull line 2 is connected to the traction plate 1, and the other end of the pull line 2 is connected to the pull line fixing device 302 of the retractor 3.

Finally, the alignment hole 304-6-1 of the upper cover 304-6 is aligned with the end portion 302-3 of the pull line fixing device 302, covering the upper cover 304-6, the positioning plate 304-6-2 at a bottom end of the upper cover 304-6 is inserted in the upper cover mounting slot 304-2-4 of the inner cover 304-2, remounting the upper cover 304-6 on the casing 304, suturing the incision, so as to complete a clinical implantation of the worm gear-worm retractor for the implanted tongue retraction device of the present invention.

When the retraction force of the pull line 2 needs to be adjusted, a special screwdriver 4 with a head shape matching a shape of the adjustment hole 301-1-1 is selected. After the special screwdriver 4 perforates skin of the mandible, the head of the special screwdriver 4 is inserted in the adjustment hole 301-1-1 through an adjustment through hole 304-1-2 on the bottom cover 304-1, and the special screwdriver 4 is turned, so that the worm 301-1 of the control switch 301 is rotated to drive the worm gear 301-2 to rotate.

Thus, the pull line 2 is loosened or tensioned to adjust the retraction force of the pull line 2. When the worm 301-1 rotates in the right-hand screw direction, the worm gear 301-2 rotates clockwise to tension the pull line 2, so that the retraction force increases; when the worm 301-1 rotates in the left-hand screw direction, the worm gear 301-2 rotates counter-clockwise to loosen the pull line 2, so that the retraction force decreases.

The retractor 3 is made of a medical material, thereby ensuring good biocompatibility of the retractor 3 after the retractor 3 is implanted into a human body.

The worm gear-worm retractor used in the implanted tongue retraction device of the present invention, includes the control switch 301 capable of adjusting the retraction force of the pull line 2, the pull line fixing device 302 capable of fixing the pull line 2 and the casing 304; the control switch 301 and the pull line fixing device 302 are mounted in the casing 304, and the control switch 301 is the worm gear-worm structure, made up of the worm 301-1 and the worm gear 301-2. Because the control switch 301 adopts the worm gear-worm structure, the worm gear 301-2 may be driven by rotating the worm 301-1, so that the pull line fixing device 302 connected to the worm gear 301-2 rotates, thereby tensioning or loosening the pull line 2 to adjust the retraction force of the pull line 2. The retractor has advantages of a compact structure, a small size and convenient adjustment.

BRIEF DESCRIPTION OF THE DRAWINGS

The aforementioned features and advantages of the invention as well as additional features and advantages thereof will be more clearly understood hereinafter as a result of a detailed description of preferred embodiments when taken in conjunction with the drawings.

FIG. 1 is a schematic three-dimensional structural diagram of a double worm gear retractor according to the present invention;

FIG. 2 is a front view of FIG. 1;

FIG. 3 is an A-A cross-sectional view of FIG. 2;

FIG. 4 is a schematic structural diagram of the double worm gear retractor after a bottom cover is opened according to the present invention;

FIG. 6 is a schematic structural diagram of a retractor of a single worm gear according to the present invention;

FIG. 7 is an exploded view of FIG. 6;

FIG. 11 is a top view of FIG. 9;

FIG. 12 is a B-B cross-sectional view of FIG. 11;

FIG. 13 is a C-C cross-sectional view of FIG. 12;

In the foregoing accompanying drawings:

Figure 5:
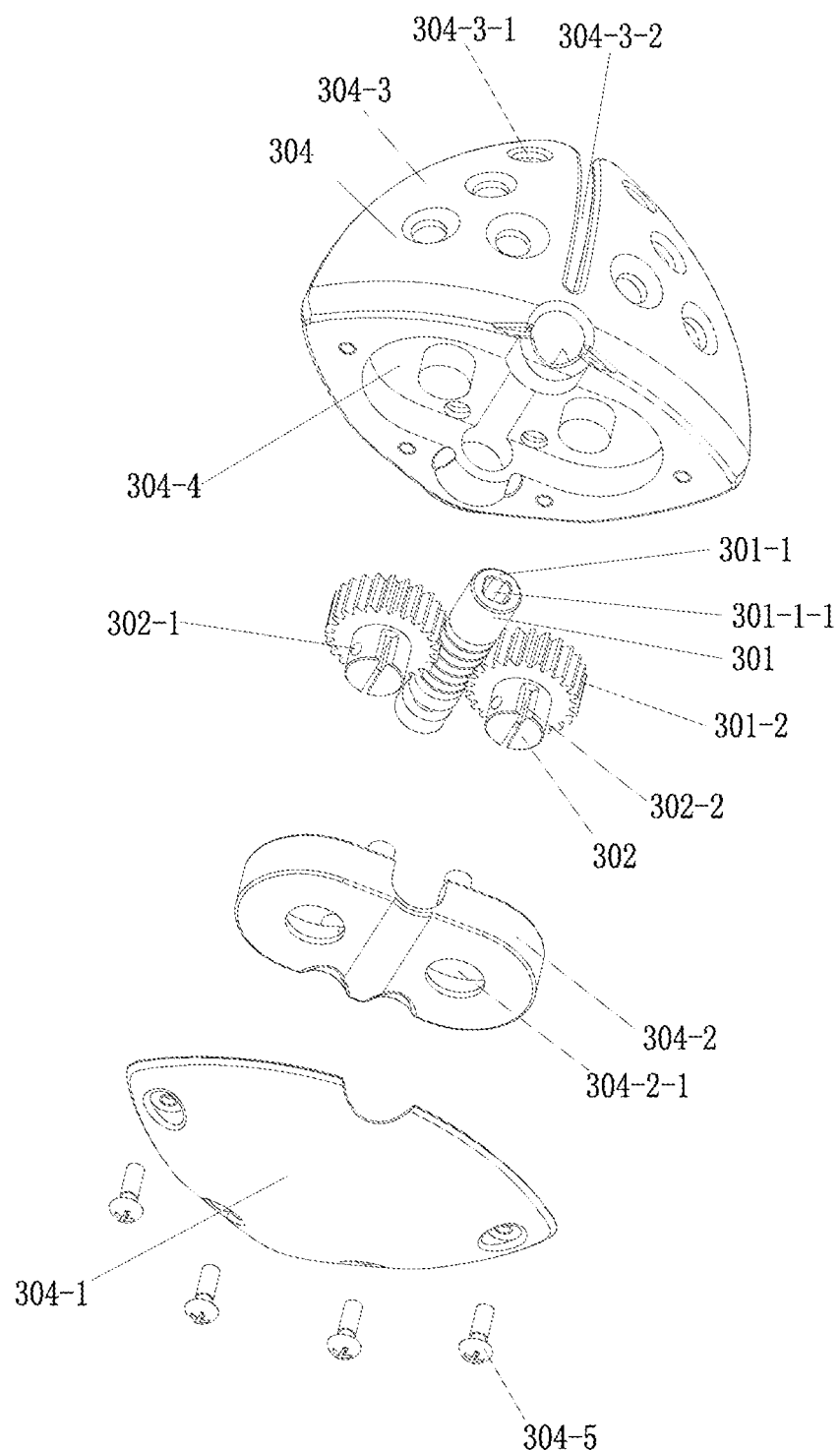
FIG. 5 is an exploded view of FIG. 1.

1 is a traction plate, 2 is a pull line, 3 is a retractor, 4 is a special screwdriver, 5 is a mandible, 9 is a tongue body, and 10 is a fixing screw.

301 is a control switch, 302 is a pull line fixing device, and 304 is a casing.

301-1 is a worm, and 301-2 is a worm gear.

302-1 is a fixing through hole for fixing the pull line, 302-2 is a line slot, and 302-3 is an end portion of the pull line fixing device.

304-1 is a bottom cover, 304-2 is an inner cover, 304-3 is a mandible front fixing plate, 304-4 is a mounting slot, 304-5 is a screw, and 304-6 is an upper cover.

301-1-1 is an adjustment hole of the worm; 304-1-1 is a bottom screw through hole through which the screw passes on the bottom cover, 304-1-2 is an adjustment through hole through which a screwdriver passes, 304-2-1 is a through hole through which the pull line fixing device passes on the inner cover, 304-2-2 is a mounting hole through which the screw passes on the inner cover, 304-2-3 is a positioning end at which the pull line fixing device is positioned, and 304-2-4 is a mounting slot of the upper cover; 304-2-31 is a pull line through hole through which the pull line passes, 304-2-32 is a positioning hole of the pull line fixing device, and 304-2-33 is a mounting slot in which the pull line fixing device is mounted; 304-3-1 is a front screw through hole through which a fixing screw passes on a fixing plate, and 304-3-2 is a slot hole of the mandible front fixing plate; 304-6-1 is an alignment hole and 304-6-2 is a positioning plate.

Like reference numerals refer to corresponding parts throughout the several views of the drawings.

DESCRIPTION OF EMBODIMENTS

Reference will now be made in detail to embodiments, examples of which are illustrated in the accompanying drawings. In the following detailed description, numerous specific details are set forth in order to provide a thorough understanding of the subject matter presented herein. But it will be apparent to one skilled in the art that the subject matter may be practiced without these specific details. In other instances, well-known methods, procedures, components, and circuits have not been described in detail so as not to unnecessarily obscure aspects of the embodiments.

Embodiment 1: a Double Worm Gear Retractor for an Implanted Tongue Retraction Device of the Present Invention Refer to FIG. 1 to FIG. 5, in this embodiment, a retractor 3 includes a control switch 301 capable of adjusting a retraction force of a pull line 2, a pull line fixing device 302 capable of fixing the pull line 2 and a casing 304. The control switch 301 and the pull line fixing device 302 are mounted in the casing 304.

The control switch 301 is a worm gear-worm structure formed by a worm 301-1 and a worm gear 301-2. When the worm 301-1 is rotated, the worm gear 301-2 may be driven to rotate clockwise or counter-clockwise. The pull line fixing device 302 is disposed on the worm gear 301-2.

The casing 304 includes an inner cover 304-2, the control switch 301 is mounted on the casing 304 through the inner cover 304-2, and the pull line fixing device 302 connected to the worm gear 301-2 extends out through a through hole 304-2-1 on the inner cover 304-2. In the technical solution that uses the exposed pull line fixing device 302 and the concealed worm gear and worm, on the one hand, it is convenient to mount the pull line 2, and on the other hand, protected by the inner cover 304-2, the worm gear-worm structure is mounted in a mounting slot between the casing 304 and the inner cover 304-2, so a risk that the pull line 2 is twisted and torn apart by the worm gear-worm structure because of slippage and displacement is avoided.

The casing 304 includes a bottom cover 304-1, and the control switch 301 and the pull line fixing device 302 are mounted in the bottom cover 304-1.

The control switch 301 includes at least one worm gear 301-2 and at least one worm 301-1.

In this embodiment, the control switch 301 includes two worm gears 301-2 and one worm 301-1; when the worm 301-1 rotates in a right-hand screw direction, a worm gear on a right side rotates clockwise, and a worm gear on a left side rotates counter-clockwise, to tension the pull line 2, so that a retraction force increases; when the worm 301-1 rotates in a left-hand screw direction, the worm gear on the right side rotates counter-clockwise, and the worm gear on the left side rotates clockwise, to loosen the pull line 2, so that the retraction force decreases.

The worm 301-1 has an adjustment hole 301-1-1, and the adjustment hole 301-1-1 is non-circular. The adjustment hole 301-1-1 is usually a polygonal hole, for example, a triangular hole, a square hole, a pentagonal hole, or a hexagonal hole. The worm 301-1 can be rotated by using a special screwdriver inserted in the adjustment hole 301-1-1.

The pull line fixing device 302 includes a fixing through hole 302-1 for fixing the pull line 2 and a line slot 302-2, and a center line of the fixing through hole 302-1 is crossed with the line slot 302-2 in a three-dimensional manner. Usually, the center line of the fixing through hole 302-1 is perpendicular to the line slot 302-2.

The casing 304 includes a mandible front fixing plate 304-3; the mandible front fixing plate 304-3 has a front screw through hole 304-3-1 through which a fixing screw 10 passes and a slot hole 304-3-2; the slot hole 304-3-2 divides the mandible front fixing plate 304-3 into a left side and a right side. By adjusting a width of the slot hole 304-3-2, the mandible front fixing plate 304-3 may be applicable to different mandibular shapes, have a good shape adjustment effect and facilitate fixing of the retractor on a mandible 5.

The retractor 3 is made of a medical material.

During assembly, firstly, the control switch 301 is mounted in a mounting slot 304-4 of the casing 304, the pull line fixing device 302 connected to the worm gear 301-2 extends out through the through hole 304-2-1 on the inner cover 304-2, the inner cover 304-2 is mounted, and then the bottom cover 304-1 is fixed on the casing 304 by using a screw 304-5. Thus, the retractor 3 is assembled.

Figure 8:
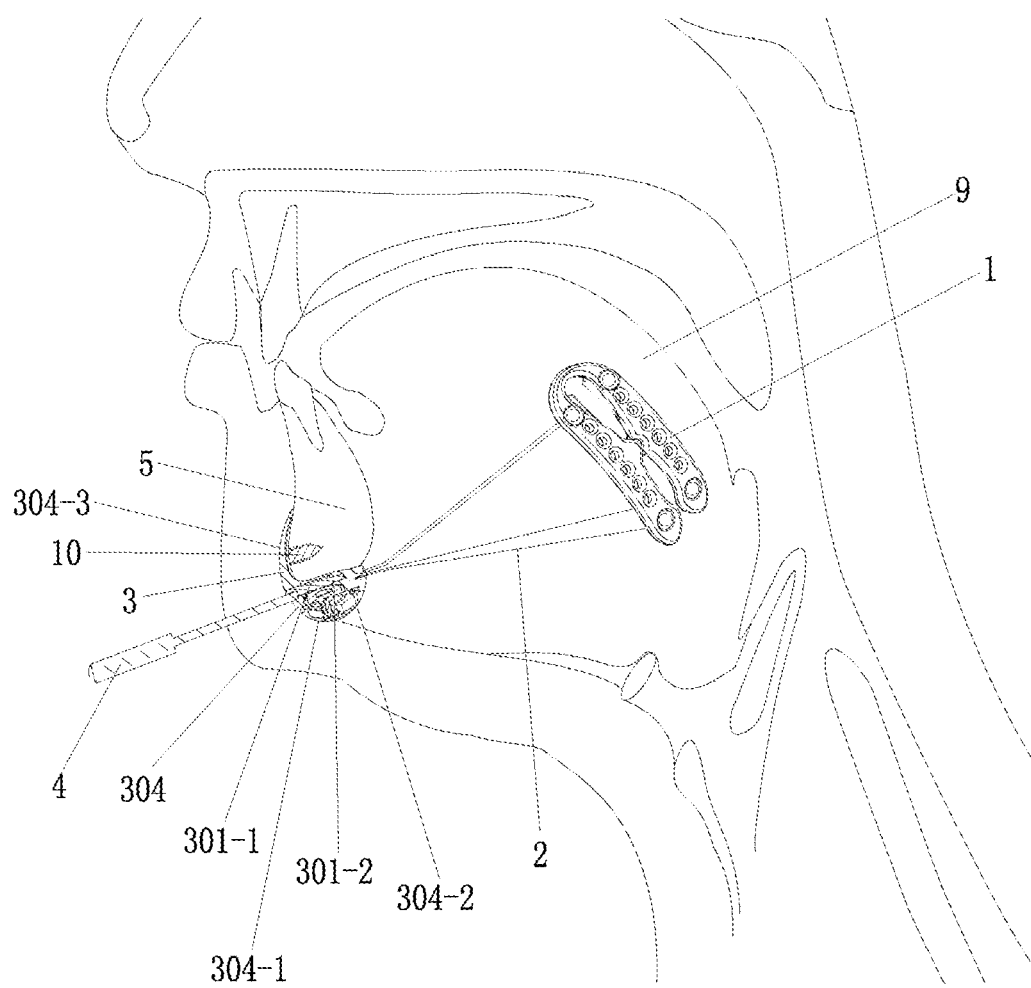
FIG. 8 is a diagram depicting a working principle of a retractor according to the present invention.

Refer to FIG. 8, when the retractor 3 is used clinically, under local anesthesia, firstly, through an oral cavity, a traction plate 1 is implanted in a tongue body 9 near a glossopharyngeal portion by cutting a small incision at a tongue dorsum portion. Then, a small incision of approximately 6 mm is cut at a bottom portion of the mandible 5, the mandible front fixing plate 304-3 of the retractor 3 is fixed on the mandible 5 by using the fixing screw 10 similar to a bone screw structure, that is, the retractor 3 is fixed on the mandible 5; in this case, the mandible front fixing plate 304-3 is in front of the mandible 5, and a main body of the retractor 3, that is, the casing 304 mounted with the worm gear-worm structure, is suspended at the bottom portion of the mandible 5. Next, the pull line 2 is guided by a special instrument, through the tongue body 9, from the traction plate 1 implanted in the tongue body 9 at the tongue dorsum portion to a vicinity of the small incision in the mandible 5.

The pull line 2 is mounted and fixed on the pull line fixing device 302 connected to the worm gear 301-2 after the bottom cover 304-1 of the casing 304 is removed. The fixing through hole 302-1 and the line slot 302-2 of the pull line fixing device 302 can firmly connect the pull line 2 to the pull line fixing device 302. At this time, in the tongue body 9, one end of the pull line 2 is connected to the traction plate 1, and the other end of the pull line 2 is connected to the pull line fixing device 302 of the retractor 3.

Finally, the bottom cover 304-1 is remounted on the casing 304 by using the screw 304-5, suturing the incision, so as to complete a clinical implantation of the worm gear-worm retractor for the implanted tongue retraction device of the present invention.

When the retraction force of the pull line 2 needs to be adjusted, a special screwdriver 4 with a head shape matching a shape of the adjustment hole 301-1-1 is selected. After the special screwdriver 4 perforates skin of the mandible, the head of the special screwdriver 4 is inserted in the adjustment hole 301-1-1, and the special screwdriver 4 is turned, so that the worm 301-1 of the control switch 301 is rotated to drive the worm gear 301-2 to rotate. Thus, the pull line 2 is loosened or tensioned to adjust the retraction force of the pull line 2. When the worm 301-1 rotates in the right-hand screw direction, the worm gear on the right side rotates clockwise, and the worm gear on the left side rotates counter-clockwise, to tension the pull line 2, so that the retraction force increases; when the worm 301-1 rotates in the left-hand screw direction, the worm gear on the right side rotates counter-clockwise, and the worm gear on the left side rotates clockwise, to loosen the pull line 2, so that the retraction force decreases.

The worm gear-worm retractor for the implanted tongue retraction device of the present invention, has advantages of a compact structure, a small size and convenient adjustment.

In this embodiment, only the structure of the retractor in which the worm gear-worm structure are formed by one worm 301-1 and two worm gears 301-2 of the present invention is described exemplarily. However, the worm gear-worm structure of the worm gear-worm retractor for the implanted tongue retraction device of the present invention may further have other combinations of quantity of the worm gears and the worms.

A worm gear-worm structure formed by one worm 301-1 and one worm gear 301-2 has an advantage of a smaller size. Refer to FIG. 6 and FIG. 7, in this embodiment, the control switch 301 only includes one worm gear 301-2 and one worm 301-1. The worm gear 301-2 can be driven by rotating the worm 301-1, so that the pull line fixing device 302 connected to the worm gear 301-2 rotates, to tension or loosen the pull line 2 to adjust the retraction force of the pull line 2.

Embodiment 2: an Inlaid Double Worm Gear Retractor for an Implanted Tongue Retraction Device of the Present Invention Refer to FIG. 9 to FIG. 17, the difference between this embodiment and Embodiment 1 is that, in this embodiment, the worm gear 301-1 and the worm 301-2 of the retractor 3 are embedded in a mounting slot at a front side of the mandible 5. Compared with Embodiment 1, in this embodiment, a maxillofacial appearance of a patient does not change significantly after a surgery.

Refer to FIG. 9 to FIG. 16, in this embodiment, the control switch 301 includes one worm gear 301-2 and one worm 301-1; when the worm 301-1 rotates in the right-hand screw direction, the worm gear 301-2 rotates clockwise, to tension the pull line 2, so that the retraction force increases; when the worm 301-1 rotates in the left-hand screw direction, the worm gear 301-2 rotates counter-clockwise, to loosen the pull line 2, so that the retraction force decreases.

Figure 9:
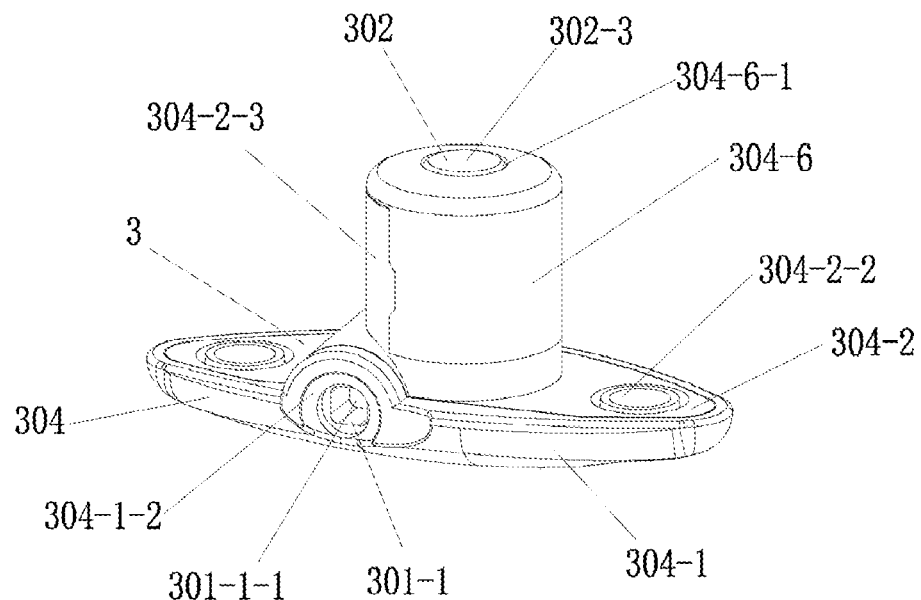
FIG. 9 is a schematic structural diagram of an embedded single worm gear retractor according to the present invention.

In this embodiment, a casing 304 further includes an upper cover 304-6; the upper cover 304-6 has an alignment hole 304-6-1. The alignment hole 304-6-1 matches a size with an end portion 302-3 of a pull line fixing device 302. Refer to FIG. 9.

Figure 10:
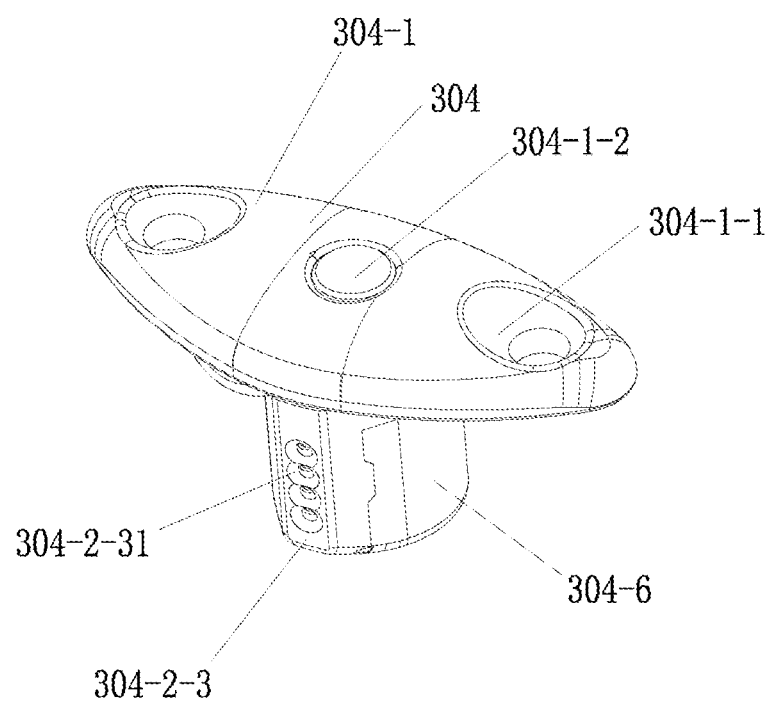
FIG. 10 is a schematic structural diagram of FIG. 9 in a bottom view.
Figure 14:
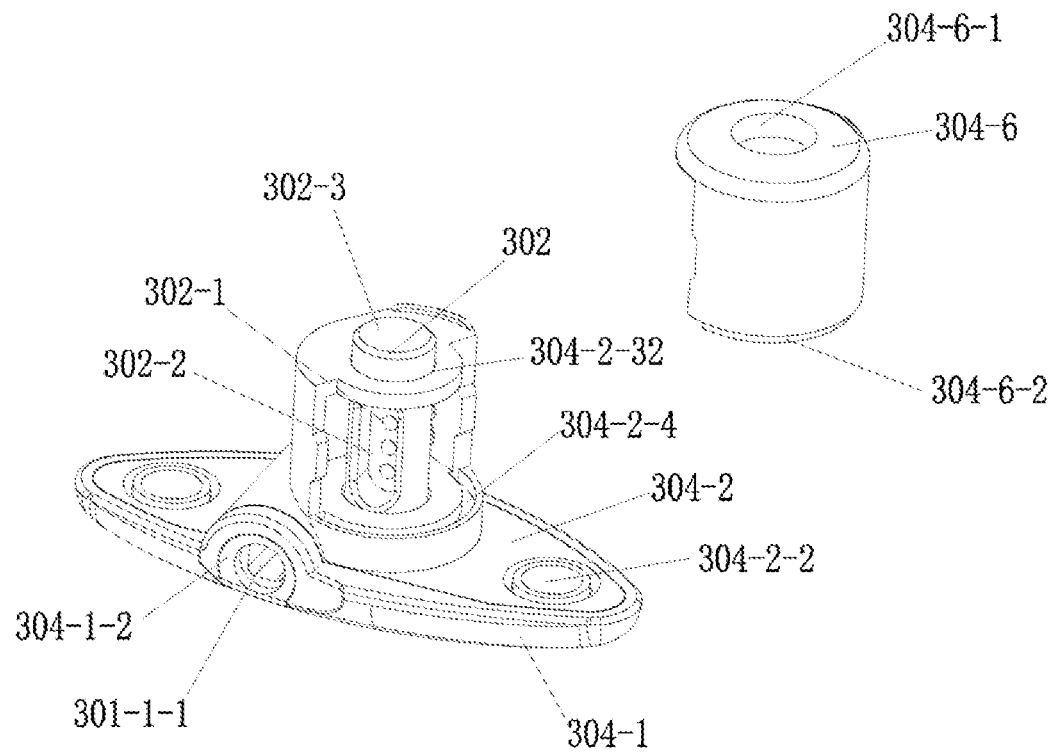
FIG. 14 is a schematic structural diagram of the retractor after an upper cover is opened in a front view.
Figure 15:
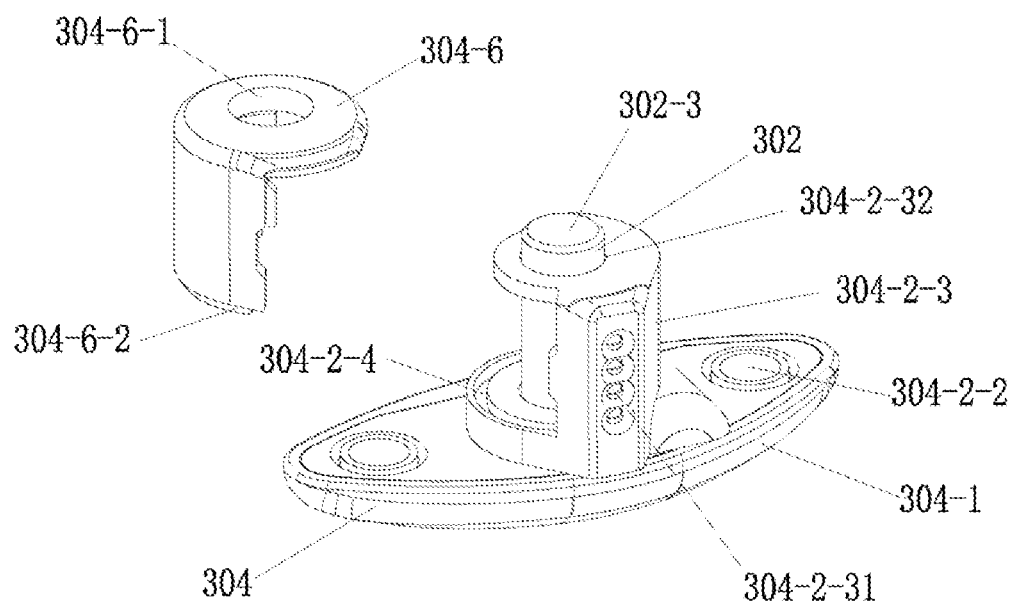
FIG. 15 is a rear view of FIG. 14.
Figure 16:
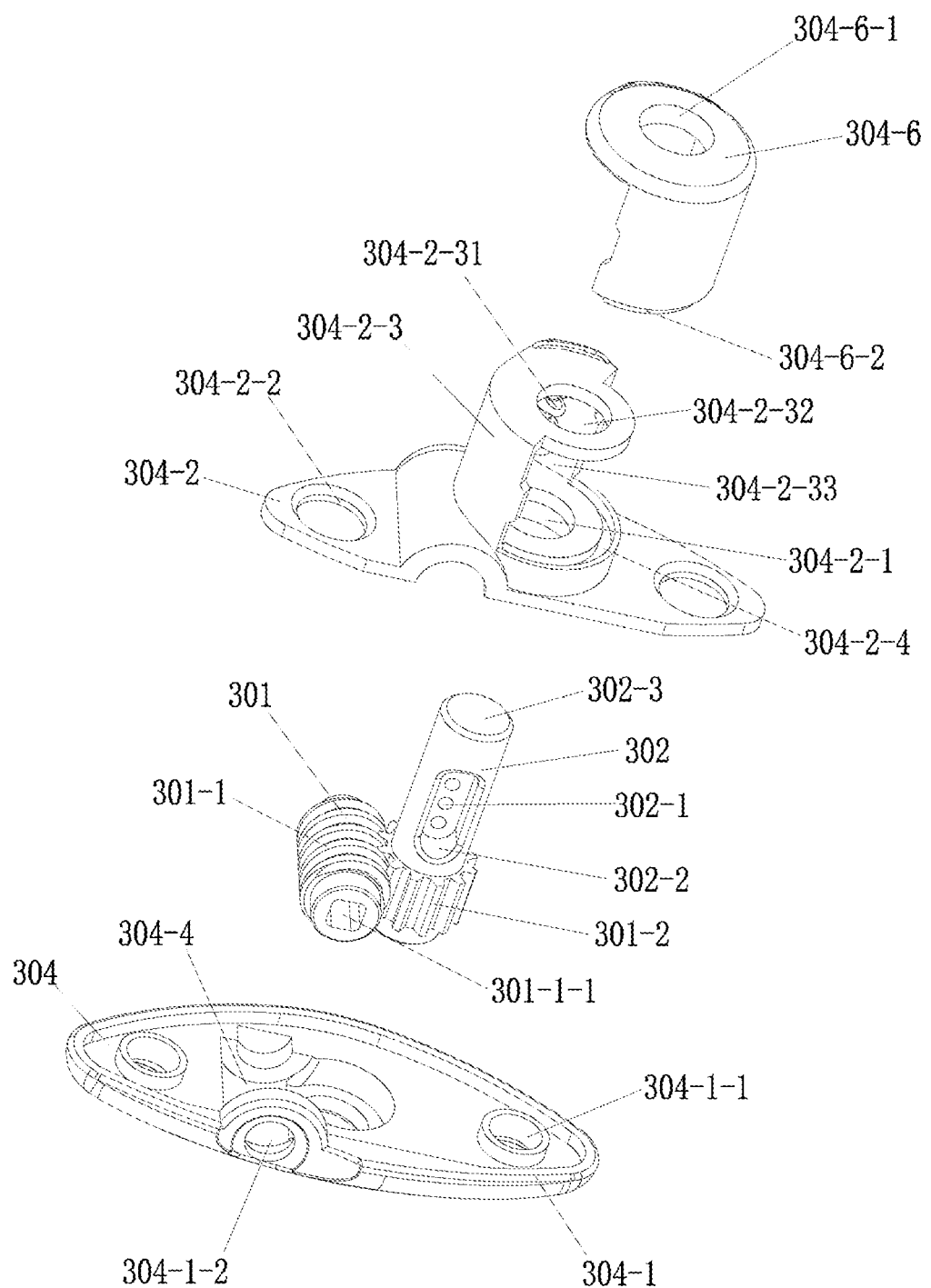
FIG. 16 is an exploded view of FIG. 9.

The bottom cover 304-1 has a bottom screw through hole 304-1-1 through which the fixing screw 10 passes, as shown in FIG. 10.

The inner cover 304-2 has a through hole 304-2-1 through which the pull line fixing device 302 passes, a mounting hole 304-2-2 through which the fixing screw 10 passes, and a positioning end 304-2-3 at which the pull line fixing device 302 is positioned. The positioning end 304-2-3 has a pull line through hole 304-2-31 through which the pull line 2 passes, and a positioning hole 304-2-32 through which the pull line fixing device 302 is positioned. After the pull line fixing device 302 connected to the worm gear 301-2 passes through the through hole 304-2-1 on the inner cover 304-2, the pull line fixing device 302 is mounted in a mounting slot 304-2-33 of the positioning end 304-2-3, and positioned through the positioning hole 304-2-32, as shown in FIG. 11 to FIG. 16.

The retractor 3 is made of a medical material, thereby ensuring good biocompatibility of the retractor 3 after the retractor 3 is implanted into a human body.

During assembly, firstly, the control switch 301 formed by the worm gear 301-2 and the worm 301-1 is mounted in the mounting slot 304-4 of the casing 304. Then, the inner cover 304-2 is mounted, after the pull line fixing device 302 connected to the worm gear 301-2 extends out through the through hole 304-2-1 on the inner cover 304-2, the pull line fixing device 302 is mounted in the mounting slot 304-2-33 of the positioning end 304-2-3, and is positioned through the positioning hole 304-2-32. Then, the alignment hole 304-6-1 on the upper cover 304-6 is aligned with the end portion 302-3 of the pull line fixing device 302, covering the upper cover 304-6, a positioning plate 304-6-2 of a bottom end of the upper cover 304-6 is inserted in an upper cover mounting slot 304-2-4 of the inner cover 304-2 to complete an assembly of the retractor 3.

Figure 17:
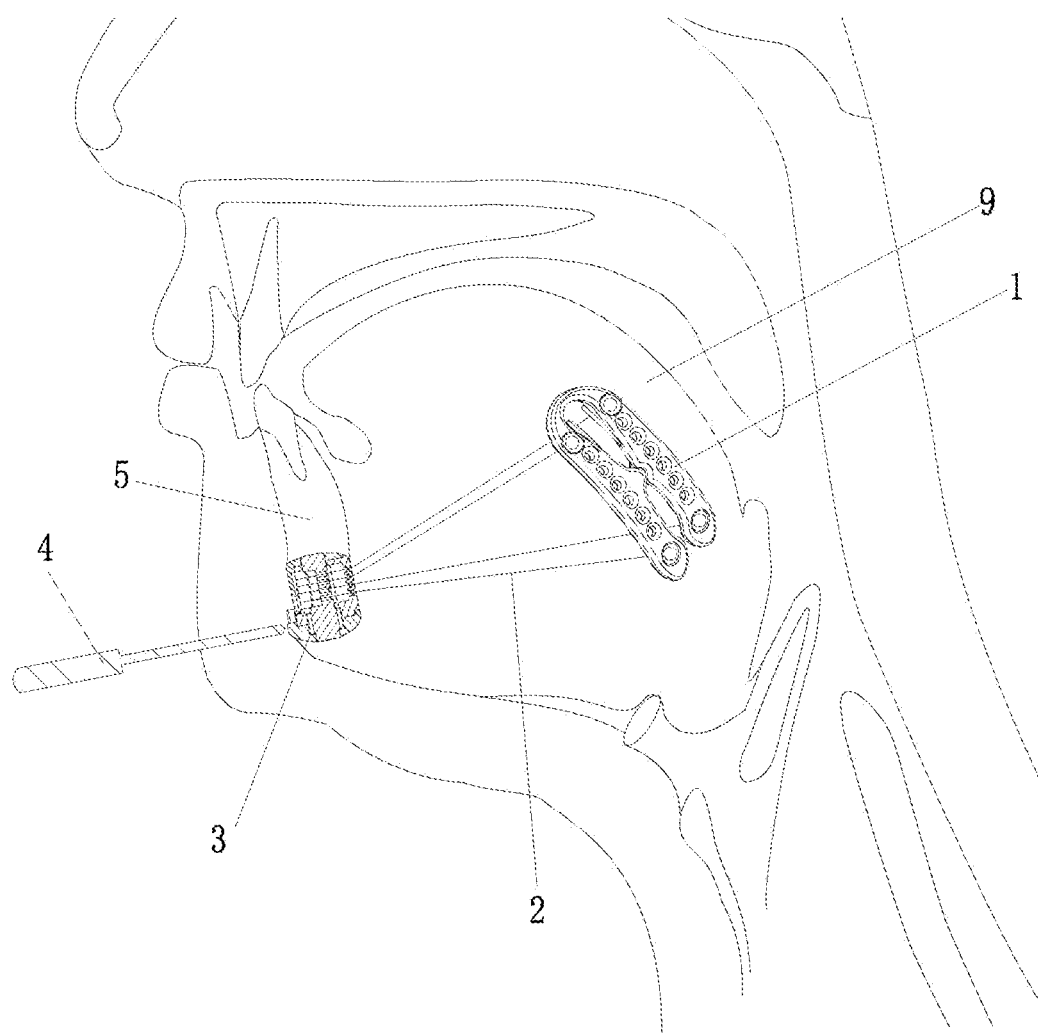
FIG. 17 is a diagram depicting a working principle of the embedded single worm gear retractor according to the present invention.

Refer to FIG. 17, when the retractor 3 is used clinically, under local anesthesia, firstly, through an oral cavity, the traction plate 1 is implanted in a tongue body 9 near a glossopharyngeal portion by cutting a small incision at a tongue dorsum portion. Then, a mounting slot having a width of about 8 mm and a depth of about 8 mm is cut in a middle portion of the mandible 5, and the retractor 3 is fixed on the mandible 5 through the through hole 304-1-1 on the bottom cover 304-1 and the mounting hole 304-2-2 on the inner cover 304-2 by using the fixing screw 10 similar to a bone screw structure. In this case, the pull line fixing device 302 connected to the worm gear 301-2 and the positioning end 304-2-3 of the inner cover 304-2 are embedded in the mounting slot in front of the mandible 5, and other parts of the retractor 3 are suspended at a bottom portion of the mandible 5. Next, the pull line 2 is guided by a special instrument, through the tongue body 9, from the traction plate 1 implanted in the tongue body 9 at the tongue dorsum portion to a vicinity of the small incision in the mandible 5.

The pull line 2 is mounted and fixed on the pull line fixing device 302 connected to the worm gear 301-2 after the bottom cover 304-6 of the casing 304 is removed. The fixing through hole 302-1 and the line slot 302-2 of the pull line fixing device 302 can firmly connect the pull line 2 to the pull line fixing device 302. At this time, in the tongue body 9, one end of the pull line 2 is connected to the traction plate 1, and the other end of the pull line 2 is connected to the pull line fixing device 302 of the retractor 3.

Finally, the alignment hole 304-6-1 of the upper cover 304-6 is aligned with the end portion 302-3 of the pull line fixing device 302, covering the upper cover 304-6, the positioning plate 304-6-2 at a bottom end of the upper cover 304-6 is inserted in the upper cover mounting slot 304-2-4 of the inner cover 304-2, remounting the upper cover 304-6 on the casing 304, suturing the incision, so as to complete a clinical implantation of the worm gear-worm retractor for the implanted tongue retraction device of the present invention.

When the retraction force of the pull line 2 needs to be adjusted, a special screwdriver 4 with a head shape matching a shape of the adjustment hole 301-1-1 is selected. After the special screwdriver 4 perforates skin of the mandible, the head of the special screwdriver 4 is inserted in the adjustment hole 301-1-1, and the special screwdriver 4 is turned, so that the worm 301-1 of the control switch 301 is rotated to drive the worm gear 301-2 to rotate. Thus, the pull line 2 is loosened or tensioned to adjust the retraction force of the pull line 2. When the worm 301-1 rotates in the right-hand screw direction, the worm gear 301-2 rotates clockwise to tension the pull line 2, so that the retraction force increases; when the worm 301-1 rotates in the left-hand screw direction, the worm gear 301-2 rotates counter-clockwise to loosen the pull line 2, so that the retraction force decreases.

In this embodiment, because there is only one worm 301-1 and one worm gear 301-2, the retractor is smaller in size, and trauma is less in a surgical procedure. Furthermore, a mounting slot is cut in a center of a front side of the mandible 5, and the positioning end 304-2-3 of the inner cover 304-2 and the pull line fixing device 302 mounted inside are embedded together in the mounting slot of the mandible 5, thereby decreasing a height of a mandible implanted device as much as possible. Therefore, a maxillofacial appearance of a patient does not change significantly by adjusting a size of the bottom cover 304-1 properly. Compared with Embodiment 1, in this embodiment, the patient has better appearance after the surgery.

It should be noted that, the structures disclosed and described in the present invention may be replaced by other structures with the same effect, and meanwhile embodiments of the present invention described herein are not the sole structure to implement the present invention. Though preferred embodiments of the present invention have been introduced and described in the specification, persons skilled in the art should know that these embodiments are merely described by way of example, and persons skilled in the art may make various changes, improvements, and replacements without departing from the present invention. Therefore, the protection scope of the present invention should be defined in accordance with the spirit and scope of the appended claims of the present invention.

While particular embodiments are described above, it will be understood it is not intended to limit the invention to these particular embodiments. On the contrary, the invention includes alternatives, modifications and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, operations, elements, and/or components, but do not preclude the presence or addition of one or more other features, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

Although some of the various drawings illustrate a number of logical stages in a particular order, stages that are not order dependent may be reordered and other stages may be combined or broken out. While some reordering or other groupings are specifically mentioned, others will be obvious to those of ordinary skill in the art and so do not present an exhaustive list of alternatives. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

The invention claimed is:

1. A device for implantation to reduce sleep apnea, comprising:
   a worm drive assembly, including:
      a worm having a longitudinal axis and a spiral thread positioned on a surface of the worm along the longitudinal axis; and
      a worm wheel rotatably coupled to the worm, wherein teeth of the worm wheel engage with the spiral thread of the worm and the worm wheel has a rotation axis that intersects the longitudinal axis of the worm;
   a pull line fixing device fixedly positioned on a first surface of the worm wheel and configured to rotate with the worm wheel about the rotation axis simultaneously, the pull line fixing device including a fixing through hole and a line slot, wherein a center line of the fixing through hole is crossed with the line slot in a three-dimensional manner and the center line of the fixing through hole is perpendicular to the line slot; and
   a pull line connected to the pull line fixing device by securing the pull line to the pull line fixing device via the fixing through hole and the line slot, wherein:
      during operation of the device, a rotation of the worm about the longitudinal axis causes (i) a corresponding rotation of the worm wheel and the pull line fixing device about the rotation axis and (ii) a winding/unwinding of the pull line on the pull line fixing device, thereby adjusting a tension of the pull line.

2. The device according to claim 1, wherein:
   the worm wheel is a first worm wheel; and
   the worm drive assembly includes a second worm wheel rotatably coupled to the worm, wherein:
      teeth of the second worm wheel engage with the spiral thread of the worm;
      the second worm wheel has a rotation axis that intersects the longitudinal axis of the worm; and
      the first worm wheel and the second worm wheel are separated by the worm.

3. The device according to claim 1, wherein: the worm has an adjustment hole, and the adjustment hole is non-circular.

4. The device according to claim 1, wherein:
   when the worm rotates in a right-hand screw direction, the worm wheel rotates clockwise to tension the pull line, thereby increasing a retraction force; and
   when the worm rotates in a left-hand screw direction, the worm wheel rotates counter-clockwise to loosen the pull line, thereby decreasing the retraction force.

5. The device according to claim 1, wherein the device is made of a medical material.

6. The device according to claim 1, further comprising:
   a casing, wherein the worm drive assembly and the pull line fixing device are positioned in the casing.

7. The device according to claim 6, wherein:
   the casing includes an inner cover with a first through hole;
   the worm drive assembly is mounted on the casing via the inner cover; and
   the pull line fixing device extends out of the first through hole.

8. The device according to claim 6, wherein:
   the casing includes a bottom cover; and
   the worm drive assembly and the pull line fixing device are mounted in the bottom cover.

9. The device according to claim 6, wherein:
   the casing comprises a mandible front fixing plate; and
   the mandible front fixing plate has a front screw through hole through which a fixing screw passes and a slot hole, wherein the slot hole divides the mandible front fixing plate into a left side and a right side.

10. The device according to claim 6, wherein:
    the casing comprises an upper cover with an alignment hole.

11. The device according to claim 8, wherein: the bottom cover has a bottom screw through hole through which a fixing screw passes.

12. The device according to claim 7, wherein:
    the inner cover further has a mounting hole through which a fixing screw passes and a positioning end at which the pull line fixing device is positioned;

the positioning end has a pull line through hole through which the pull line passes and a positioning hole through which the pull line fixing device is positioned; and the pull line fixing device is mounted in a mounting slot of the positioning end after extending out of the through hole on the inner cover, and is positioned through the positioning hole.

13. The device according to claim 2, wherein:

when the worm rotates in a right-hand screw direction, the first worm wheel rotates clockwise and the second worm wheel rotates counter-clockwise to tension the pull line, thereby increasing a retraction force; and when the worm rotates in a left-hand screw direction, the first worm wheel on rotates counter-clockwise and the second worm wheel rotates clockwise to loosen the pull line, thereby decreasing the retraction force.

\* \* \* \* \*